United States Patent [19]

Barnard et al.

[11] Patent Number: 4,561,310

[45] Date of Patent: Dec. 31, 1985

[54] FLUID FLOW MEASUREMENT

[75] Inventors: Richard H. Barnard, St. Albans; Terence P. Stock, Bishops Stortford, both of England

[73] Assignee: ITT Industries, Inc., New York, N.Y.

[21] Appl. No.: 576,994

[22] Filed: Feb. 6, 1984

[30] Foreign Application Priority Data

Feb. 11, 1983 [GB] United Kingdom ............... 8303885

[51] Int. Cl.$^4$ ........................... G01F 1/32; G01F 1/86
[52] U.S. Cl. ................... 73/861.02; 73/861.24
[58] Field of Search ........... 73/861.02, 861.03, 861.22, 73/861.24, 653, 656; 250/227; 350/96.15, 96.29

[56] References Cited

U.S. PATENT DOCUMENTS

| | | | |
|---|---|---|---|
| 1,935,445 | 11/1933 | Heinz | 73/861.24 |
| 3,116,639 | 1/1964 | Bird | 73/861.24 |
| 3,719,073 | 3/1973 | Mahon | 73/861.22 |
| 3,776,033 | 12/1973 | Herzl | 73/861.22 |
| 3,888,120 | 6/1975 | Burgess | 73/861.24 |
| 4,048,854 | 9/1977 | Herzl | 73/861.02 |
| 4,206,642 | 6/1980 | Bearcroft | 73/861.24 |
| 4,247,764 | 1/1981 | Kissinger | 250/227 X |
| 4,281,553 | 8/1981 | Datta-Barua | 73/861.24 |
| 4,433,238 | 2/1984 | Adolfsson et al. | 250/227 |
| 4,472,022 | 9/1984 | Bearcroft et al. | 73/861.24 X |

*Primary Examiner*—Herbert Goldstein
*Attorney, Agent, or Firm*—T. L. Peterson; R. C. Turner

[57] ABSTRACT

An instrument for measuring simultaneously the flow rate and density of a moving fluid includes means for measuring the frequency and amplitude of vortices shed by interaction of the fluid with a bluff body. Typically the sensing means includes an optical fibre movable in response to pressure changes in the fluid. Computation of the mass flow rate of the fluid can be effected.

In one embodiment a light signal from a transmitter (41) is modulated via a sensor (42) and is then fed via a detector (45) and A to D converter (46) to a microprocessor (47) where demodulation and computation of mass flow rate is effected. The microprocessor also provides neative feedback to maintain the output level of the transmitter substantially constant.

1 Claim, 5 Drawing Figures

FLUID FLOW MEASUREMENT

This invention relates to fluid measurement devices, and in particular for arrangements for mass flow metering of fluids.

A number of techniques have been devised for the measurement of fluid flow. There is an increasing need for the measurement of mass flow rate and, where the fluid is of known constant density, this is simple to achieve by multiplying the flow rate by a calibration constant. Where however the fluid density is not known, or varies with time, e.g. when the fluid comprises a slurry, present techniques cannot readily provide the necessary information.

The object of the present invention is to minimise or to overcome this disadvantage.

According to one aspect of the invention there is provided an instrument for measuring simultaneously the flow rate and the density of a fluid, the instrument including means for modulating a light signal with a frequency and amplitude corresponding to the frequency and amplitude of vortices shed by interaction of the fluid with a bluff body disposed therein, means for determining from said modulation a measure of the volume flow rate of the fluid, and feedback control means whereby the light carrier signal on which said modulation is superimposed is maintained at a substantially constant level.

According to another aspect of the invention there is provided an instrument for measuring the mass flow rate of the moving fluid, the instrument including means for generating vortices in the fluid, a pressure sensor disposed in the fluid and responsive to the pressure fluctuations associated with the vortices, means whereby the sensor modulates a light signal with a signal whose frequency and amplitude correspond respectively to the fluid flow rate and the product of fluid flow rate squared and the density, means for demodulating the light signal, and means for calculating from the flow rate and density signals a measure of the mass flow rate of the fluid.

To accomplish mass flow measurement it is necessary to determine the product RV where V is the fluid flow speed and R is the fluid density.

We have found that a vortex flowmeter can, with calibration, provide signals corresponding to $RV^2$ and V and hence by division RV can be determined. The volume flow ($V_F$), is derived from the normal mode of vortex flowmeter operation and is determined from flow velocity V derived from the expression $$V = fd/s$$

where f is the vortex shedding frequency, d the bluff body width and s the Strouhal number. Over the range of Reynolds number encountered in normal pipe flow measurement the Strouhal number is substantially constant so volume flow $V_F$ is given by $V_F = VA$ where A is the pipe cross sectional area, i.e.

$$V_F = (fd/s)A$$

Since A is also a constant, volume flow is proportional to the vortex shedding frequency.

The quantity $RV^2$ can be derived from a measure of the standard deviation of the pressure fluctuations DP incident on a pressure sensor and induced by vortex shedding. This pressure is related to density by $DP = KRV^2$ where K is a calibration constant.

Since the mass flow Q is given by $Q = RV_F$ we have $Q = (kDP/f)$ where k is a further calibration constant.

Hence, by measurements of both the vortex frequency F and amplitude, which is proportional to DP, it is possible, once the value of the calibration constant k has been determined, to derive a measure of the mass flow Q of the fluid.

The arrangements described herein are all intended for use with a vortex detector of the type in which a light signal is modulated in correspondence with the frequency at which vorteces are shed from a bluff body by the moving fluid. Typically we employ vortex detectors of the fibre optic type such as are described in our U.S. Pat. No. 4,472,022 although the techniques described herein are not of course limited to those detector arrangements.

Embodiments of the invention will now be described with reference to the accompanying drawings in which.

Figure 1:
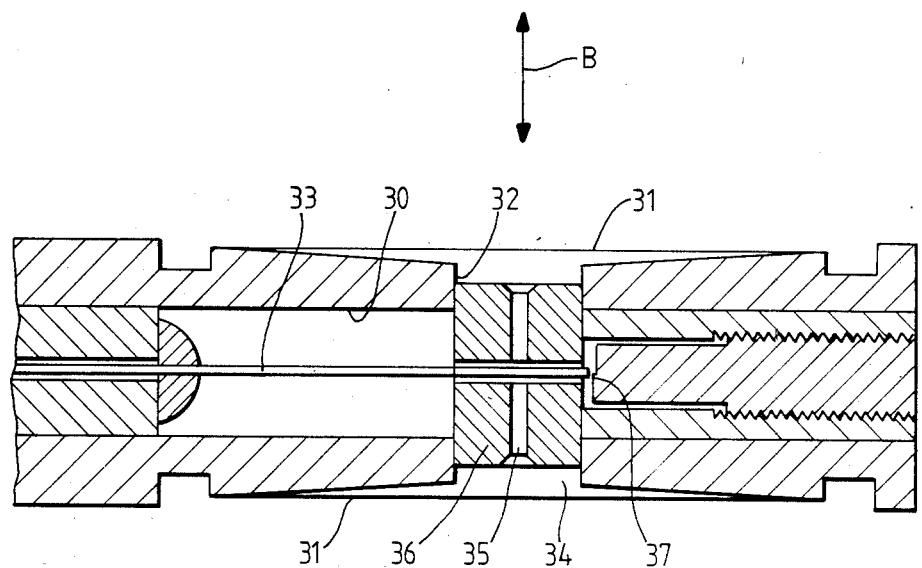
FIG. 1 is a cross-sectional view of a fibre optic fluid vortex detector.

Referring to FIG. 1, this shows a fibre optic sensor arrangement for detecting fluid pressure variations caused by vortex shedding of a moving fluid from an adjacent bluff body (not shown).

The device comprises a fully enclosed hermetically sealed sensor having a longitudinal bore 30 and a transverse bore 32. In this form of sensor the alternating pressure resulting from vortex shedding is utilised to act upon the sensor which thus constitutes a differential pressure or displacement transducer. The fluctuating differential pressure across the sensor causes diaphragms 31 to deflect, producing an oscillating flow of an incompressible filling fluid 34 through a cross port 35 in a fibre movement restriction element 36 arranged in the transverse bore 32. This flow of fluid drags an optical fibre 33 from side to side in a flapping motion in the directions indicated by double-headed arrow B thereby modulating an optical signal returned to it from a mirror/matt surface interface at 37, or alternatively a corner reflector, disposed adjacent the free fibre end. The volume of fluid passing through the cross port 35 in one half cycle is equal to that displaced by the respective diaphragm 31, and since the area of the cross port 35 is much less than that of the diaphragms, the displacement of the fluid and hence the fibre 33 will be very much larger than the displacement of the diaphragm surface. This arrangement thus provides adequate movement of the fibre with relatively small movements of the diaphragms, thus enabling a sensitive yet robust configuration to be achieved. The arrangement is more fully described in our specification No. 2,098,726.

By determining the oscillatory frequency and amplitude of the sensor the flow rate and density of the fluid can be determined. From these values the mass flow rate can then be obtained with the aid of a calibration constant related to the flow channel dimensions. This constant can be calculated or may be determined experimentally.

Figure 2:
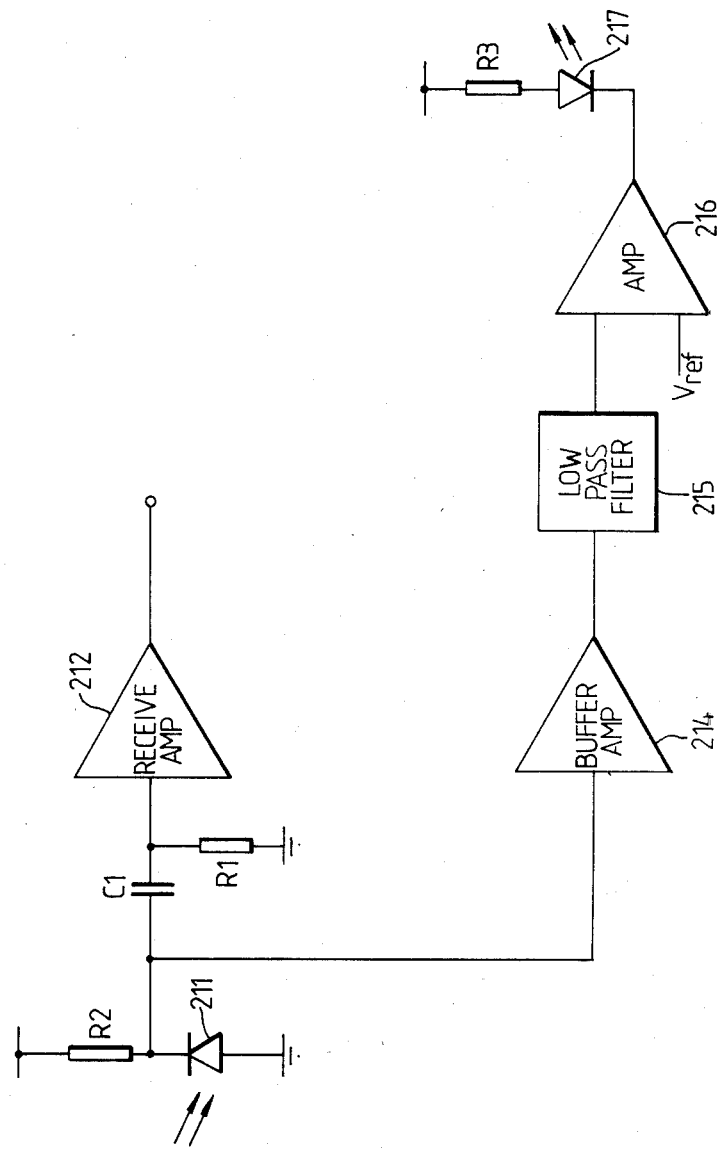
FIG. 2 is a schematic diagram of a fluid mass flow measurement arrangement.

Referring now to FIG. 2, the mass flow measurement arrangement shown includes an optical transmitter 217 whereby a light signal is transmitted to a pressure sensor, e.g. of the type shown in FIG. 1, and an optical detector 211 for receiving modulated light signals returned from the sensor. In order to ensure that the amplitude of the modulation of the return signal is a function only of the instantaneous fluid pressure a feedback loop arrangement is provided to compensate for drift in the optical system via buffer 24.

Light received by the detector 211 generates a corresponding voltage signal. This voltage signal comprises a varying signal corresponding to the fluid pressure fluctuations, whose amplitude corresponds to the fluid density and whose frequency corresponds to the flow velocity. This signal is superimposed on a bias voltage derived from voltage dividing resistors $R_1$ $R_2$ proportional to the mean light level in the return signal. The varying voltage is filtered off via capacitor C1 and is amplified by amplifier 212 to provide an output proportional to the mass flow of the fluid.

The bias voltage proportional to the mean light level at the receive amplifier input is fed via a buffer amplifier 214 and a low pass filter 215 to one input of a differential amplifier 216. The filter 215 has a cut-off frequency below the vortex frequency range, typically of 0.05 to 0.1 Hz.

The other input of the differential amplifier 216 is fed with a constant reference signal, and the output of this amplifier drives the flowmeter light source 217. The reference signal is set above the mean signal so that a decrease in the mean signal level causes an increase in light output and vice-versa.

Figure 3:
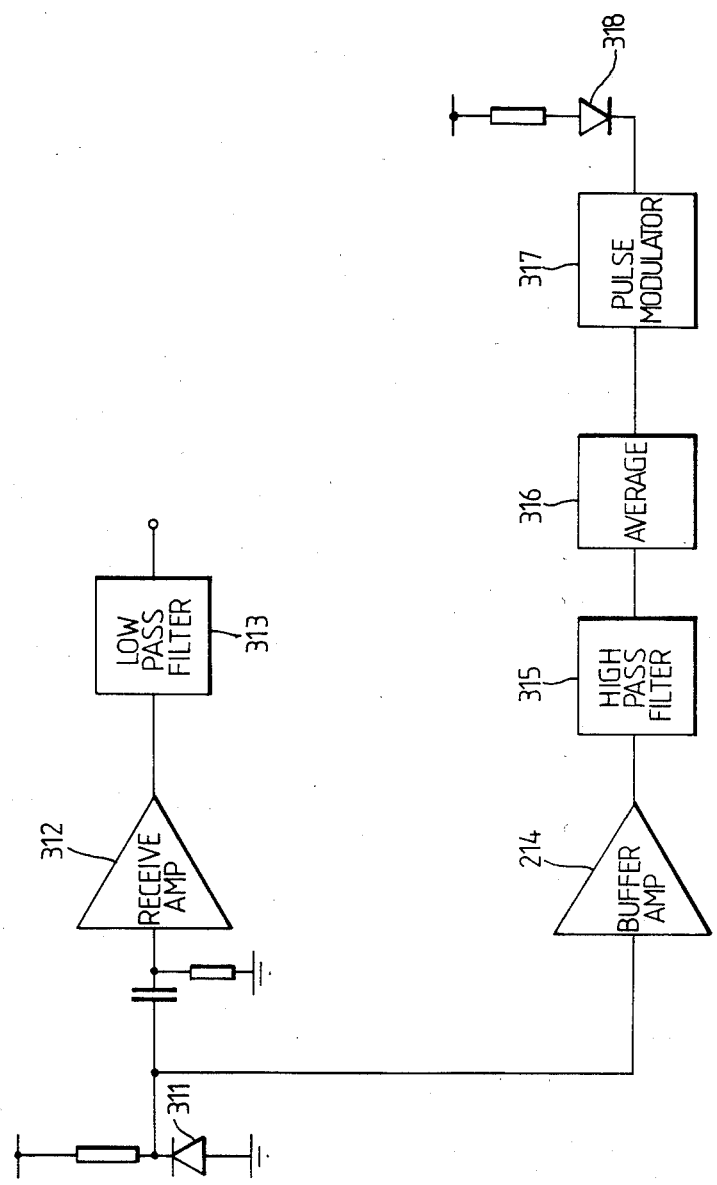
FIG. 3 is a schematic diagram of an alternative measurement arrangement.

A similar arrangement is shown in FIG. 3. In this arrangement the light signal derived from vortex pressure changes is fed via detector 311 to an amplifier 312 and a low pass filter 313 to provide a signal proportional to volume flow. The control signal is derived by high pass filtering the signal from the detector and using this filtered signal to drive a variable frequency pulse width or pulse density modulated signal via a modulation circuit 317, to the output of which the light source 318 is coupled. In some applications transient perturbations of the detector signal may be smoothed via an averaging circuit 316 connected between the high pass filter 315 and the modulator 317.

Figure 4:
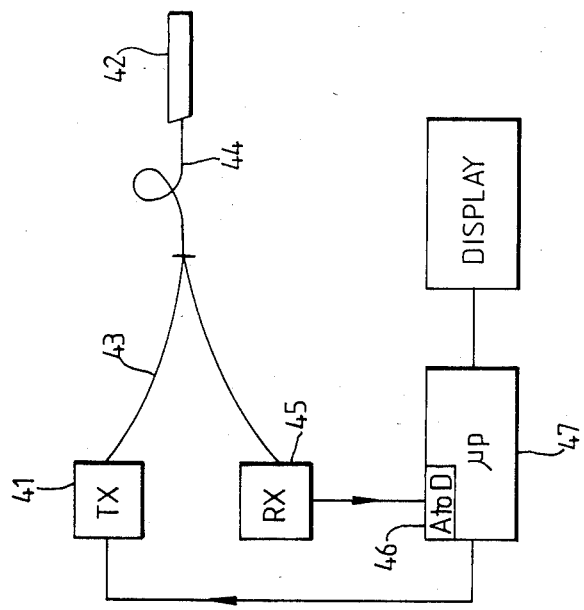

In the arrangement of FIG. 4 light from a transmitter 41 is directed to a pressure sensor 42 via optical fibres 43 and 44, and modulated light is returned to a photodetector 45. The detector output corresponding to the modulated light is fed via an analogue to digital (A to D) converter 46 to a microprocessor 47 programmed to decode the A to D output signal, thus recovering the frequency and amplitude information, and to perform the calculation necessary to obtain the mass flow rate.

Stabilization of the optical system is effected by negative feedback from the microprocessor which provides a controlling signal for the transmitter 41. This signal corresponds to the level of the carrier signal received by the detector 45.

Figure 5:
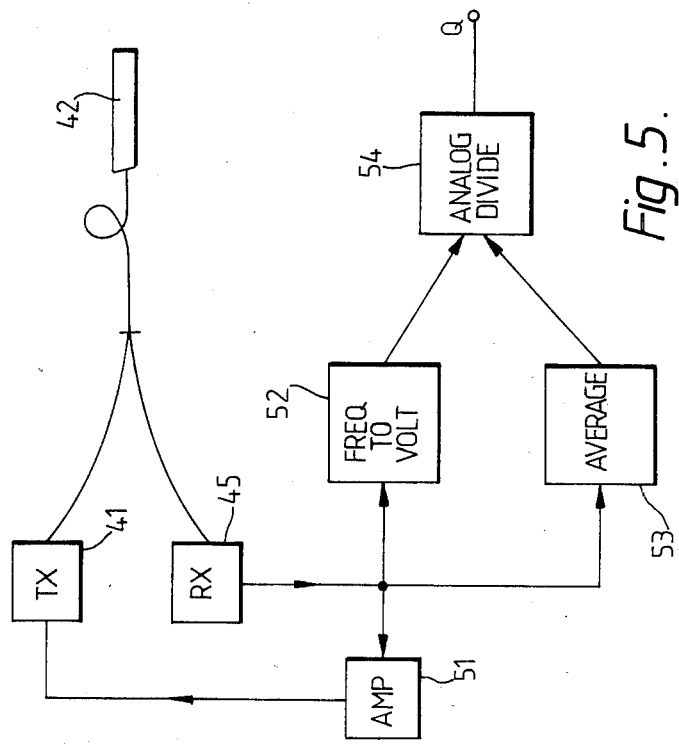
FIGS. 4 and 5 show further measurement arrangements.

A further mass flow measurement arrangement is shown in FIG. 5. The optical system is similar to that of FIG. 4 but in this arrangement negative feedback control of the transmitter 41 is effected via an amplifier 51 coupled in the feedback loop between the detector 45 and transmitter 41.

The output of the detector 45 is fed to a frequency to voltage converter 52 and to an amplitude averaging circuit 53. The converter 52 recovers the modulation on the light signal and generates an output voltage proportional to the frequency of that modulation. The amplitude averaging circuit 53 generates an output voltage proportional to the mean amplitude of the modulation signal. These two voltage signals are then fed to an analogue divider circuit 54 which produces an output quotient signal proportional to mass flow.

We claim:

1. An instrument for measuring the mass flow rate of a moving fluid, the instrument including means for generating vortices in the fluid, a pressure sensor disposed in the fluid and responsive to the pressure fluctuations associated with the vortices, means responsive to said pressure sensor for modulating a light signal with a frequency and amplitude corresponding respectively to the fluid flow velocity and the product of fluid flow velocity squared and the density, means for determining from the modulated light signal a measure of the mass flow rate of the fluid;

said modulation being affected by movement of an optical fiber in response to the vortex generation; and negative feedback control means whereby the light signal is maintained at a substantially constant level.

* * * * *